(12) United States Patent
Wang et al.

(10) Patent No.: US 9,394,535 B2
(45) Date of Patent: Jul. 19, 2016

(54) PLASMA IRRADIATION DEVICE FOR SUBSTANCE INTRODUCTION AND SUBSTANCE INTRODUCTION METHOD USING PLASMA IRRADIATION DEVICE

(75) Inventors: Douyan Wang, Kumamoto (JP); Daisuke Seki, Kumamoto (JP); Tako Namihira, Kumamoto (JP); Hisato Saito, Kumamoto (JP); Hidenori Akiyama, Kumamoto (JP)

(73) Assignee: NATIONAL UNIVERSITY CORPORATION KUMAMOTO UNIVERSITY, Kumamoto-Shi (JP)

( * ) Notice: Subject to any disclaimer, the term of this patent is extended or adjusted under 35 U.S.C. 154(b) by 590 days.

(21) Appl. No.: 13/699,564

(22) PCT Filed: May 25, 2011

(86) PCT No.: PCT/JP2011/062032
§ 371 (c)(1),
(2), (4) Date: Nov. 21, 2012

(87) PCT Pub. No.: WO2011/148996
PCT Pub. Date: Dec. 1, 2011

(65) Prior Publication Data
US 2013/0071905 A1    Mar. 21, 2013

(30) Foreign Application Priority Data

May 25, 2010  (JP) ................. 2010-119524

(51) Int. Cl.
*C12N 13/00*       (2006.01)
*C12M 1/42*        (2006.01)

(52) U.S. Cl.
CPC ............... *C12N 13/00* (2013.01); *C12M 35/04* (2013.01); *C12M 35/08* (2013.01)

(58) Field of Classification Search
CPC ...... C12M 35/04; C12M 35/02; C12M 35/08; C12N 15/87; C12N 15/02; C12N 13/00
See application file for complete search history.

(56) References Cited

U.S. PATENT DOCUMENTS 7,608,839 B2 * 10/2009  Coulombe et al. ............ 250/426
2003/0229202 A1  12/2003  Guo et al.

(Continued)

FOREIGN PATENT DOCUMENTS

EP     1 849 798 A1    10/2007
JP     2004-512275 A    4/2004

(Continued)

OTHER PUBLICATIONS

Leveille, V. et al; Design and preliminary characterization of a miniature pulsed FR APGD torch with downstream injection of the source of reactive species, 2005, Plasma Sources Sci. Technol., 14, p. 467-476.*

(Continued)

*Primary Examiner* — William H Beisner
*Assistant Examiner* — Danielle Henkel
(74) *Attorney, Agent, or Firm* — Birch, Stewart, Kolasch & Birch, LLP

(57) ABSTRACT

Disclosed is a liquid culture medium for substance introduction, which is capable of increasing the survival rate of cells after substance introduction as much as possible when the cells are irradiated with plasma for the purpose of introducing a target substance into each of the cells. Specifically disclosed is a liquid culture medium for substance introduction, which is used for the purpose of introducing a predetermined target substance into a cell and enables introduction of the target substance into the cell by having the cell in the liquid culture medium, which contains the target substance, irradiated with a plasma jet. The liquid culture medium contains a damage preventing component that prevents the cell from damage due to the plasma jet.

4 Claims, 8 Drawing Sheets

(56) References Cited

U.S. PATENT DOCUMENTS

2004/0110297 A1 6/2004 Miyoshi et al.
2009/0039790 A1* 2/2009 Suslov .................... 315/111.21

FOREIGN PATENT DOCUMENTS

| JP | 2006-219435 A | 8/2006 |
|---|---|---|
| WO | WO 02/064767 A1 | 8/2002 |
| WO | WO 2004/015101 A1 | 2/2004 |

OTHER PUBLICATIONS

International Search Report, issued in PCT/JP2011/062032, dated Jul. 5, 2011.

Leduc et al., "Cell permeabilization using a non-thermal plasma", New Journal of Physics, vol. 11 (2009), pp. 1-12.

* cited by examiner

PLASMA IRRADIATION DEVICE FOR SUBSTANCE INTRODUCTION AND SUBSTANCE INTRODUCTION METHOD USING PLASMA IRRADIATION DEVICE

TECHNICAL FIELD

The present invention relates to a liquid culture medium for substance introduction and a method for introducing a substance into cells.

BACKGROUND TECHNOLOGY

Hitherto, a method for the introduction of a substance of interest into a cell has been proposed, which comprises a dropwise addition of a liquid solution containing a substance sought to be introduced (hereafter called also a "target substance") into a cell and irradiation of the cells with a plasma generated by a plasma generator (for example, refer to Patent Document No. 1).

This method enables the target substance to be present in the cell.

PRIOR ART REFERENCE

Patent Document No. 1: WO2002/064767

SUMMARY OF THE INVENTION

Problems to be Solved by the Invention

The conventional method for the substance introduction, however, is likely to cause cells to be damaged by the irradiation of plasma so that a survival rate of cells after the plasma irradiation (after the substance introduction) cannot be said to be high.

With the above background technology taken into consideration, the present invention provides a liquid culture medium for substance introduction that is capable of increasing the survival rate of cells after the substance introduction as much as possible upon irradiation of cells with plasma for the purpose of introducing the target substance into the cell. The present invention also provides a method for introducing the substance into a cell, which can increase the survival rate of the cells after the substance introduction as much as possible.

Means for Solving the Problems

In order to solve the problems underlying the conventional method, a first embodiment of the present invention provides a liquid culture medium for introducing a predetermined target substance into a cell, which is capable of introducing the target substance into the cell by the irradiation of the cell in the liquid culture medium with a plasma jet, which contains the target substance and a damage preventing component that prevents the cell from damage due to the plasma jet.

The present invention in a $2^{nd}$ embodiment is characterized in that the damage preventing component to be contained in the liquid culture medium as described in the first embodiment is a protein having an absorbance at a wavelength of 200 nm to 300 nm.

The present invention in a $3^{rd}$ embodiment is characterized in that the damage preventing component contained in the liquid culture medium as described in the first embodiment is a mixture of plural kinds of proteins having an absorbance at the wavelength of 200 nm to 300 nm.

The present invention in a $4^{th}$ embodiment is characterized in that the mixture of plural kinds of the proteins contained in the liquid culture medium as described in the $3^{rd}$ embodiment is fetal bovine serum.

The present invention in a $5^{th}$ embodiment provides the method for the substance introduction into the cell, which introduces the target substance into the cell by irradiating the cell of a culture container with the plasma jet, which contains the liquid culture medium with the predetermined target substance described in any of the embodiments 1 to 4.

The present invention in a $6^{th}$ embodiment is characterized in that, in the method for the substance introduction as described in the $5^{th}$ embodiment, the plasma jet is generated from a plasma generator generating the plasma jet and the plasma generator comprises an observation section for observing cells in the culture container, a plasma generation section for generating the plasma jet, and a micromanipulator section for supporting the plasma generation section movably in a three-dimensional direction.

The present invention in a $7^{th}$ embodiment is characterized in that, in the method for the substance introduction as described in the $6^{th}$ embodiment, the plasma generation section is constituted by a tubular dielectric which comprises a tube member disposed therein so as to allow a gas stream containing a noble gas as a main component to flow therethrough freely and a double-pole electrode disposed at a constant interval on the outer peripheral surface of the tube member, wherein the plasma jet is generated from an opening at one end of the tube member by sending a low-frequency high-voltage to each of the electrodes from a low-frequency high-voltage electric source and generating electric discharges within the tube member.

The present invention in an $8^{th}$ embodiment is characterized in that, in the method for the substance introduction as described in the $5^{th}$, $6^{th}$, and $7^{th}$ embodiments, the target molecule is at least one selected from a polypeptide, a polynucleotide and an antibody.

The present invention in a $9^{th}$ embodiment is characterized in that, in the method for the substance introduction as described in the $8^{th}$ embodiment, said polypeptide or said antibody is connected to a transmembrane signal sequence for facilitating a transmembrane through a cell membrane.

The present invention in a $10^{th}$ embodiment uses fetal bovine serum as the damage preventing component for the cell for the purpose to prevent the cell from the damage to be caused by the plasma jet upon introduction of the predetermined target molecule contained in the liquid culture medium by irradiating the cells growing in the liquid culture medium with the plasma jet.

Effects of the Invention

The liquid culture medium for the introduction of the predetermined target substance into the cell according to the present invention as described in the first embodiment enables the introduction of the target substance into the cell by irradiating the cell in the liquid culture medium with the plasma jet, which contains the target substance and the damage preventing component capable of preventing damages of the cells due to the plasma jet, thereby increasing the survival rate of the cells as much as possible after the substance introduction upon the plasma irradiation for the purpose of introducing the target substance into the cell.

The present invention as described in the $2^{nd}$ embodiment can prevent the cells from damages because ultraviolet rays radiated from the plasma jet are absorbed by the damage preventing component that is constituted by a protein demonstrating an absorbance at the wavelength of 200 to 300 nm.

The present invention as described in the 3$^{rd}$ embodiment can prevent the cells from damages because the damage preventing component consisting of the mixture of plural kinds of proteins demonstrating an absorbance at the wavelength of 200 to 300 nm can absorb the ultraviolet rays radiated from the plasma jet.

The present invention as described in the 4$^{th}$ embodiment can grow the cells while preventing the cells from damages because the mixture of plural kinds of proteins consisting of fetal bovine serum can absorb the ultraviolet rays radiated from the plasma jet.

The present invention as described in the 5$^{th}$ embodiment provides the method for the substance introduction into the cell, which can increase the survival rate of the cells after the substance introduction as much as possible due to the fact that the target substance is introduced into the cell by subjecting the cells contained in the culture container containing the liquid culture medium described above to irradiation with the plasma jet.

The present invention as described in the 6$^{th}$ embodiment can introduce the substance of interest into the cell at a pin point while confirming the predetermined cell due to the fact that the plasma jet is irradiated with the plasma jet radiated from the plasma generator and the plasma generator comprises the observation section for observing the state of the cells within the culture container, the plasma generation section for generating the plasma jet, the micromanipulator section for supporting the plasma generation section movably in a three-dimensional direction.

The present invention as described in the 7$^{th}$ embodiment can irradiate the cells with the plasma jet in a thin diameter at atmospheric pressure and at a non-thermal equilibrium because the plasma generation section is constituted by a tubular dielectric consisting of a tube member through which a gas stream containing a noble gas as a main component can flow in a free fashion and a double-pole electrode is disposed at a constant interval on the outer peripheral surface of the tube member, wherein the plasma jet is emitted from the opening at one end of the tube member by sending a low-frequency high-voltage to each of the electrodes from the low-frequency high-voltage electric source and the electric discharge is caused to occur within the tube member.

The present invention as described in the 8$^{th}$ embodiment enables at least one of the target molecules selected from the polypeptide, polynucleotide and antibody to be present in the living cells.

The present invention as described in the 9$^{th}$ embodiment can introduction the polypeptide or the antibody into the cell at a high efficiency because the transmembrane signal sequence for facilitating the transduction through the cell membrane is connected to the polypeptide or the antibody.

The present invention as described in the 10$^{th}$ embodiment can introduce the target substance into the cell while increasing the survival rate of the cells after the substance introduction as much as possible upon the irradiation for the purpose of the introduction of the target substance into the cell because fetal bovine serum is used for the damage preventing component for preventing damages caused by the plasma jet upon the introduction of the predetermined target molecule contained in the liquid culture medium by irradiating the cells growing in the liquid culture medium with the plasma jet.

BRIEF DESCRIPTION OF THE ACCOMPANYING DRAWINGS

MODES FOR CARRYING OUT THE INVENTION

Figure 1:
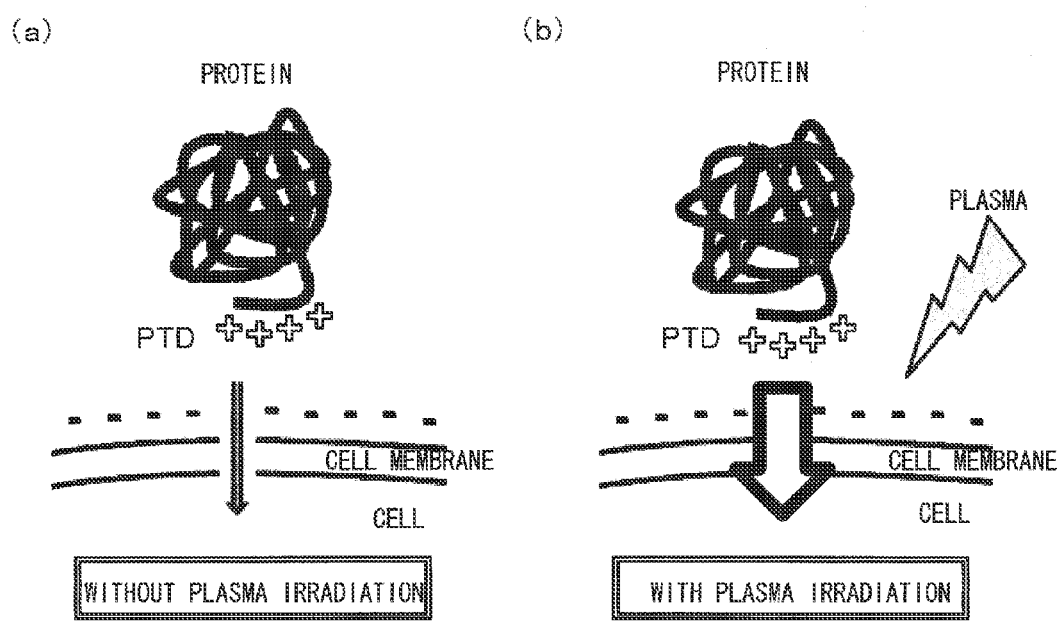
FIG. 1 is a conceptual diagram showing a method for the introduction of a protein into a cell according to a working example of the present invention.

The present invention provides a liquid culture medium for introducing a predetermined target substance into a cell.

The liquid culture medium according to a working example of the present invention enables the introduction of the target substance into the cell by irradiating the cell in the liquid culture medium containing the target substance with a plasma jet and is characterized by containing a damage preventing component capable of preventing the cell from damages due to the plasma jet.

The target substance to be used for the present invention may include, for example, a polypeptide (a protein), a polynucleotide (a nucleic acid), an antibody, an organic compound or an inorganic compound.

The liquid culture medium for containing the target substance is not limited to a particular one as long as it can at least culture cells. Therefore, it may be a minimum essential medium or a rich medium.

The term "damage" as used herein is intended to mean somewhat a damage of a cell to be caused to occur due to irradiation with a plasma jet, whichever fatal or not. The liquid culture medium according to a working example of the present invention can effectively prevent cells from damages caused by a damage factor due to the plasma jet, such as ultraviolet rays or reactive oxygen species.

The damage preventing component to be used for the present invention may include, for example, a protein demonstrating an absorbance at the wavelength of 200 nm to 300 nm. The damage preventing component may not be limited to a particular one and may include, for example, an aqueous solution containing a protein having an absorbance at the wavelength of 200 nm to 300 nm.

The damage preventing component may also include a mixture of plural kinds of proteins demonstrating an absorbance at the wavelength of 200 nm to 300 nm. The proteins in a mixed state are not limited to particular ones and part of the proteins may demonstrate an absorbance at the wavelength of 200 nm to 300 nm while the other protein may possess an absorbance that supplements the absorbance in other wavelengths. In another words, the mixture of the proteins can demonstrate an absorbance at the wavelength of 200 nm to 300 nm as a whole.

The mixture of the proteins may include, for example, fetal bovine serum (FBS). By using the fetal bovine serum as the damage preventing component, the damages of cells can be prevented from the damaging factor. Moreover, the growth of the cells can also be facilitated.

Moreover, even if the damaging factor would not become fatal in an amount or intensity of the damage to the cells by the fetal bovine serum added as the damage preventing component, there may remain some damages, although not fatal, to the cells. By using the fetal bovine serum as the damage preventing component, however, the growth of the cells can be facilitated and the recovery of the damaged cells can be furthered, thereby increasing the survival rate of the cells after the substance introduction.

The amount of the damage preventing component to be added to the culture medium may range from 1% to 10%, more preferably from 5% to 10%. If the amount of the damage preventing component would become lower than 1%, the effect of the damage prevention cannot be expected. If the amount of the damage preventing component would become higher than 10%, an increase in the damage preventing effect cannot be expected. In particular, by setting the amount of the damage preventing component to a range of from 5% to 10%, a sufficient damage preventing effect can be expected and the survival rate of the cells after the substance introduction can be further increased while a useless addition of the damage preventing component can be avoided.

The present invention provides the method for the introduction of the target substance into the cell by subjecting the cell in the culture container with the liquid culture medium containing the predetermined target substance according to a working example of the present invention to irradiation with the plasma jet.

The plasma jet may be irradiated from the plasma generator generating the plasma jet.

Especially, the plasma generator to be used for the method for the introduction of the substance into the cell according to a working example of the present invention is characterized by the observation section for observing the cells within the culture container, the plasma generation section for generating the plasma jet, and the micromanipulator section for supporting the plasma generator movably in a three-dimensional direction.

By using the plasma generator having the configuration as described above, the user can irradiate the predetermined cell with the plasma jet generating from the plasma generation section at a pin point by manipulating the micromanipulator section while observing the cells within the culture container.

Therefore, the present invention can introduce the target substance into the predetermined cell in an efficient fashion.

The plasma generation section of the plasma generator is configured by the tubular dielectric consisting of the tube member through which the noble gas flows in a free fashion and which is provided with a pair of electrodes on the outer peripheral surface of the tube member, and the plasma jet is emitted from an opening at one end of the tube member by sending a low-frequency high-voltage toward the electrodes from the low-frequency high-voltage electric source and causing the discharge to occur within the tube member.

The dielectric constituting the tube member to be used for the present invention may include, for example, a plastic such as polytetrafluoroethylene, polyethylene terephthalate, polyimde or the like, a metal oxide such as glass, quartz, silicon dioxide, aluminum oxide, zirconium oxide, titanium oxide or the like, a complex metal oxide such as barium titanate or the like. In particular, the use of glass is preferred because it can readily adjust a diameter of the tube member.

As the gas stream containing the noble gas as a major component, there may be used any gas stream as long as it contains a noble gas. As the noble gas, there may be preferably used, for example, helium or argon. The gas stream containing the noble gas as the major component may contain the noble gas as a whole or as a major component in combination with a small amount of other gas species. The gas species to be added may include, for example, oxygen (0.1 to 10%). In the event that oxygen is mixed as the other gas species, a free radical such as reactive oxygen or the like can be generated due to an oxygen plasma, thereby preventing the liquid culture medium from infection with microorganisms during the plasma irradiation.

The low frequency of the low-frequency high-voltage to be applied to the electrode may range, for example, from 1 Hz to 100 MHz. By setting the voltage at this time to approximately 1 V to 20 kV, the noble gas can be ionized to generate the plasma jet.

The application of the low-frequency high-voltage to the electrode can generate the plasma jet from an opening of the tube member. The shape and size of the opening of the tube member are not limited to particular ones and they may be determined appropriately in accordance with a width of an irradiation range of the plasma jet. In order to irradiate the plasma jet in a very narrow region, the tube member may be tapered off to the opening thereof.

In the event that a single cell is irradiated with the plasma jet at a pin point, the plasma jet of a very small size can be emitted from the opening of the tube member by setting the size of the opening thereof to 0.1 µm to 10 µm.

The plasma generator having the construction as described above can be used effectively for introducing the target substance into the cell.

As the substance capable of being introduced into the cell, there may be mentioned, for example, any substance including, but being not limited to, the polypeptide (i.e., a protein as the target substance; hereinafter also referred to as "target protein"), the polynucleotide (a nucleic acid), the antibody, a physiologically active substance, a candidate substance for medicine, and so on.

In particular, in the event that the substance to be introduced thereinto, i.e., the target substance, is the target protein or antibody, it is preferred that the transmembrane signal sequence for facilitating the transduction of the substance through the cell membrane is connected thereto.

In other words, upon introduction of the target protein or antibody, the cells in a solution containing the target protein or antibody with a protein-transduction domain (PTD) connected thereto are irradiated with the plasma jet at atmospheric pressure and at a non-thermal equilibrium to introduce the target protein or antibody into the cell, thereby allowing a very efficient presence of the target protein or antibody in the cell.

The protein-transduction domain is not limited to a particular one as long as it functions as improving the ability of transducing the target protein or antibody through the cell membrane and may include, for example, HIV-TAT (YGRKKRRQRR), ANTP (RQIKIKWPQNRRMKWKK), or the like. The capital letters enclosed by the parentheses mean an amino acid sequence of each of the protein-transduction domains. Although these protein-transduction domains are preferred to be connected to the N-terminal or C-terminal side of the predetermined protein to be introduced into the cell, it is also possible to add them to a portion other than the N-terminal or C-terminal side depending upon the kind of proteins. It is further possible to chemically connect them to an amino acid side chain (for example, SH group of cysteine or the like) constituting the protein to be introduced into the cell using a crosslinking agent.

Although it is known that the target protein or antibody with the PTD added thereto may become likely to be introduced into the cell, it cannot be said to be introduced efficiently into the cell.

For instance, as shown in FIG. 1(a), in the event that the target protein with the PTD added thereto is introduced without use of plasma, the PTD of the target protein charged positively and the cell membrane charged negatively pull against each other so that an efficiency of introduction is very poor.

On the other hand, as shown in FIG. 1(b), in the event that the plasma jet is irradiated, electrons contained in the plasma jet are allowed to adhere to the cell membrane, thereby instantaneously causing an opening in the cell membrane and allowing the target protein gathered together around the cells to readily pass through the cell membrane by means of a force by which the PTD and the cell membrane pull against each other. This can dramatically improve an efficiency of introduction of the substance into the cell.

The density of the plasma jet to be irradiated toward the cells is not limited to a particular one and it may be acceptable as long as the plasma jet may not become excessive to such an extent to cause damages against the survival of cells.

The following is a description regarding a working example of the liquid culture medium for introducing the substance into the cell and the method for the substance introduction according to the present invention by explaining the construction of the plasma generator and referring to the accompanying drawings.

(Preparation of a Vector)

Figure 2:
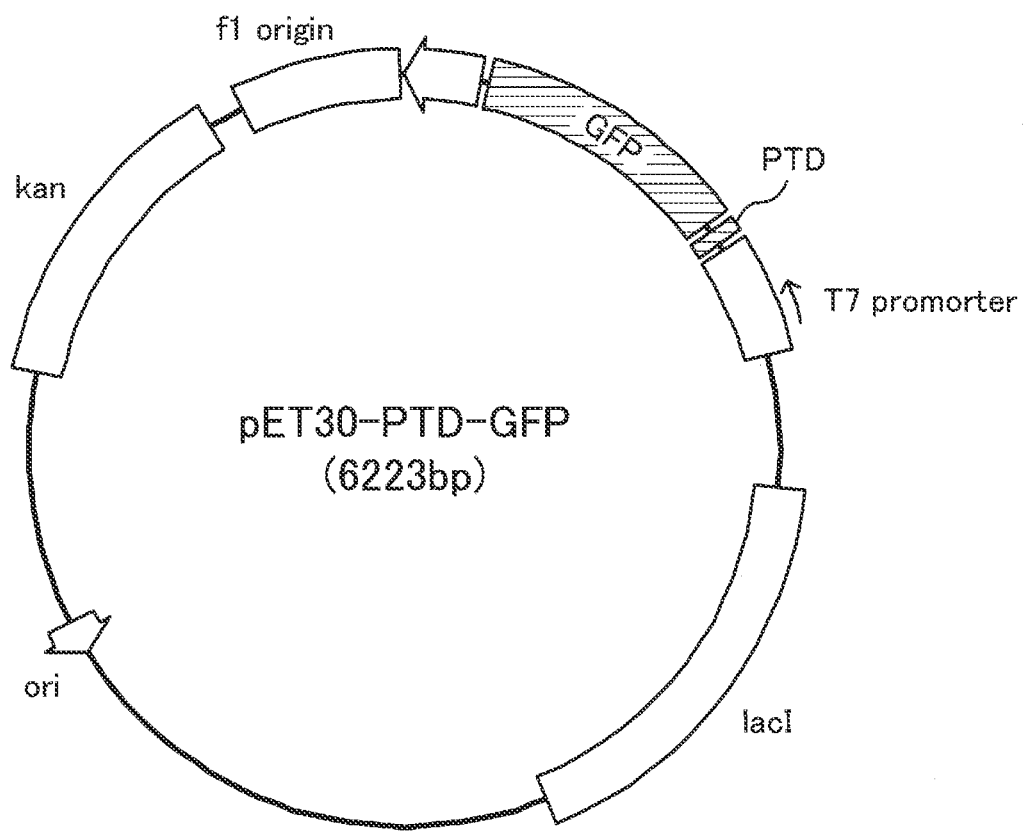
FIG. 2 is an explanatory illustration showing an expression vector for expressing a protein to be introduced into a cell.

A DNA fragment (33 bp) encoding a PTD composed of 11R (a recurring sequence of 11 arginine bases) and a green fluorescent protein (GFP) gene were inserted into a multi-cloning site of an expression vector (see FIG. 2). As the expression vector, there was used pET30 (Novagen). The constructed vector (pET30-PTD-GFP) was cloned and its base sequence was determined to confirm the insertion of the DNA fragment encoding the PTD and the GFP gene at the predetermined position.

(Transformation and Expression)

Next, the expression vector prepared above was then transformed by introducing it into *E. coli* BL21 (DE3) strain as a host, and the strain was incubated in a Luria-Bertani (LB) medium for 18 hours.

The cultured host *E. coli* BL21 (DE3) was collected by centrifuging it at 13,000×g for three minutes and, after appropriate washing, subjected to ultrasonic treatment in a physiological saline to give a host extract solution which in turn was used as a crude enzyme solution for experiments for introducing a protein into a cell as will be described hereinafter.

(Experiments for Introducing a Target Protein into a Cell)

A PTD-connected GFP was then introduced into a cell. For brevity of explanation, a description will be made hereinafter, first, regarding the structure of the plasma generator for generating the plasma jet and, then, regarding details of the experiment for the introduction of the target protein.

(Structure of Plasma Generator)

Figure 3:
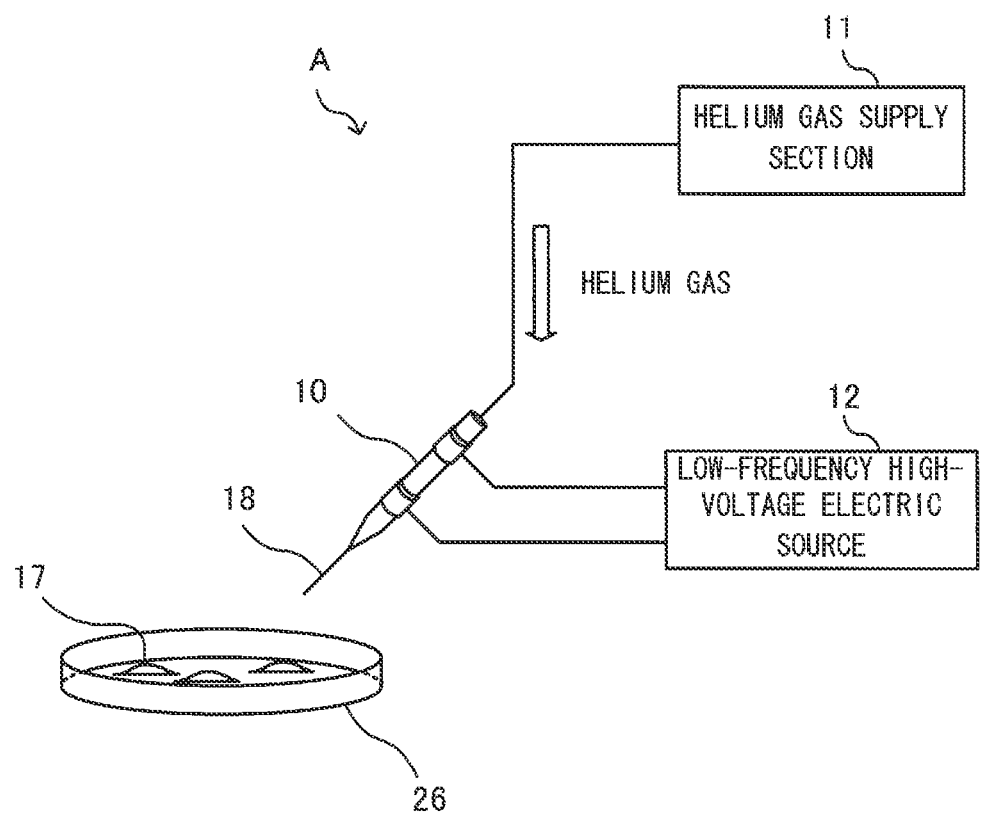
FIG. 3 is an explanatory illustration showing a structure of a plasma generator.

As shown in FIG. 3, a plasma generator A to be used for this experiment comprises an electrode section 10 for generating a plasma, a helium gas supply section 11 for supplying the electrode section with helium gas, and a low-frequency high-voltage electric source section 12 for supplying the electrode section with a low-frequency high-voltage.

This plasma generator A supplies the electrode section 10 with helium gas from the helium gas supply section 11 and applies the low-frequency high-voltage thereto from the low-frequency high-voltage electric source 12, generating a plasma jet and irradiating cells 17 within a culture container 26 with the plasma jet.

Figure 4:
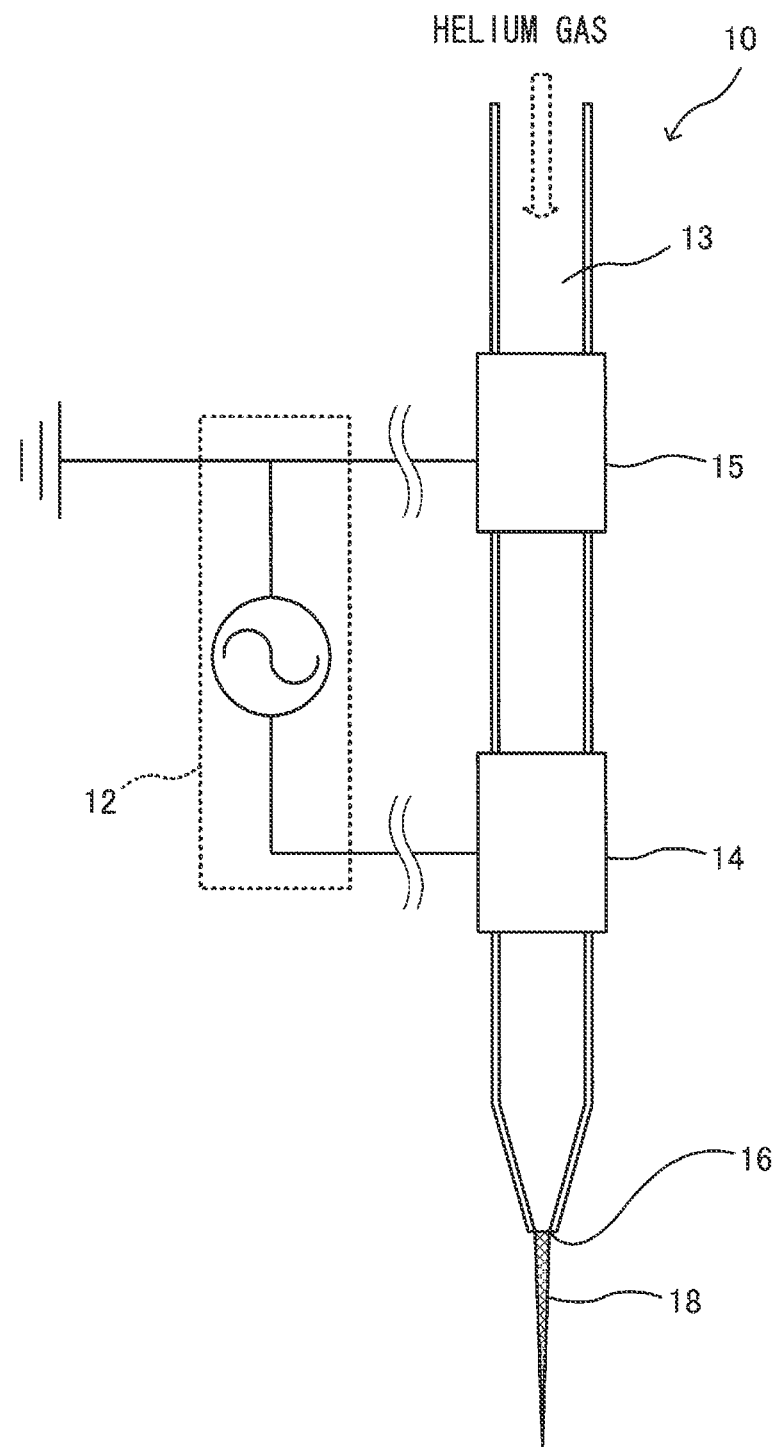
FIG. 4 is an explanatory illustration showing a structure of an electrode section.

As shown in FIG. 4, the electrode section 10 is made of glass and comprises a tube member 13 with its tip portion tapered off and first and second electrodes 14 and 15 are disposed at a constant interval, respectively, on an outer peripheral surface of the tube member 13.

The tube member 13 is connected at its one end to the helium gas supply section 11 and helium gas supplied from the helium gas supply section 11 flows through the tube member 13.

The other end of the tube member 13 forms an opening 16 tapered off to a point and helium gas is emitting from the opening 16. The tube member 13 with its one end portion tapered off can be manufactured by heating the one end portion of a glass tube circumferentially and pulling the glass tube in a red hot state in both directions. By changing the position at which the tapered glass tube is cut off, the tube member 13 can be formed so as to have an opening size as desired.

The first electrode 14 is an electrode that is disposed coaxially nearby the opening 16 of the tube member 13 and connected electrically to the low-frequency high-voltage electric source 12. The second electrode 15 is disposed coaxially with the tube member 13 at a position remote from the opening compared to the first electrode 14 and connected to the ground.

In other words, the second electrode 15 as a grounding electrode is disposed at the upstream side of helium gas flowing through the tube member 13 and the first electrode 14 as a low-frequency high-voltage electrode is disposed at the downstream side thereof.

The plasma jet 18 can be emitted from the tip of the opening 16 by flowing helium gas through the tube member 13 and applying the low-frequency high-voltage between the first and second electrodes 14 and 15, respectively.

(Introduction of Protein into Cell)

Experiments were carried out for introducing the PTD-connected GFP and a non-PTD-connected GFP, respectively, into HeLa cells incubated for three days in a D-MEM+5% FBS culture medium. For a comparative purpose, three samples were prepared: test sample 1 using a liquid culture medium for the substance introduction according to a working example of the present invention, test sample 2 for a comparison and test sample 3 using a liquid culture medium for the substance introduction according to another working example of the present invention. Each of the samples was prepared in a way as described hereinafter.

Test Sample 1:

The test sample 1 was prepared by adding 100 μl of the liquid culture medium for the substance introduction according to a working example of the present invention, except the medium within the culture container in which HeLa cells were incubated. This liquid culture medium contained 100 μg/ml of the PTD-connected GFP as a target substance and D-MEM (pH 8.0) containing 5% fetal bovine serum (FBS) as a damage preventing component.

Test Sample 2:

The test sample 2 contained 100 μg/ml of the non-PTD-connected GFP and 100 μl of D-MEM (pH 8.0) containing no fetal bovine serum (FBS), except the medium within the culture container in which HeLa cells were incubated.

Test Sample 3:

The test sample 3 contained 100 μg/ml of the non-PTD-connected GFP and 100 μl of D-MEM (pH 8.0) containing 5% fetal bovine serum (FBS), except the medium within the culture container in which HeLa cells were incubated.

Each of the test samples was irradiated with the plasma jet generated by the plasma generator A for 30 seconds and a rate of death of cells was computed after test. Each of the tests was carried out by supplying the electrode section 10 with helium gas in 3.0 liter per minute while generating plasma by applying low-frequency high-voltage in 10 kV at 10 kHz.

The test results revealed that the test samples 1 and 3, each containing the damage preventing component, showed a decrease in the number of living cells after irradiation with the plasma jet by approximately 24 to 29% compared to the number of living cells before irradiation.

On the other hand, the test results revealed that the test sample 2 containing no damage preventing component showed a decrease in the considerable number of living cells after irradiation with the plasma jet by approximately 56% compared to the number of living cells before irradiation.

These phenomena are considered to be caused to occur by generation of some reactive oxygen species or ultraviolet rays in a buffer solution by the irradiation with the plasma jet causing damages in cells. In other words, the damage preventing component (FBS as used herein) is considered to play a role for protecting the cells from these reactive oxygen species or ultraviolet rays.

Therefore, the irradiation of the cells with the plasma jet in the presence of the damage preventing component enables the introduction of the target substance into the cell while preventing the cells from damages to be caused by the reactive oxygen species even if the cells are present in a solution.

Figure 5:
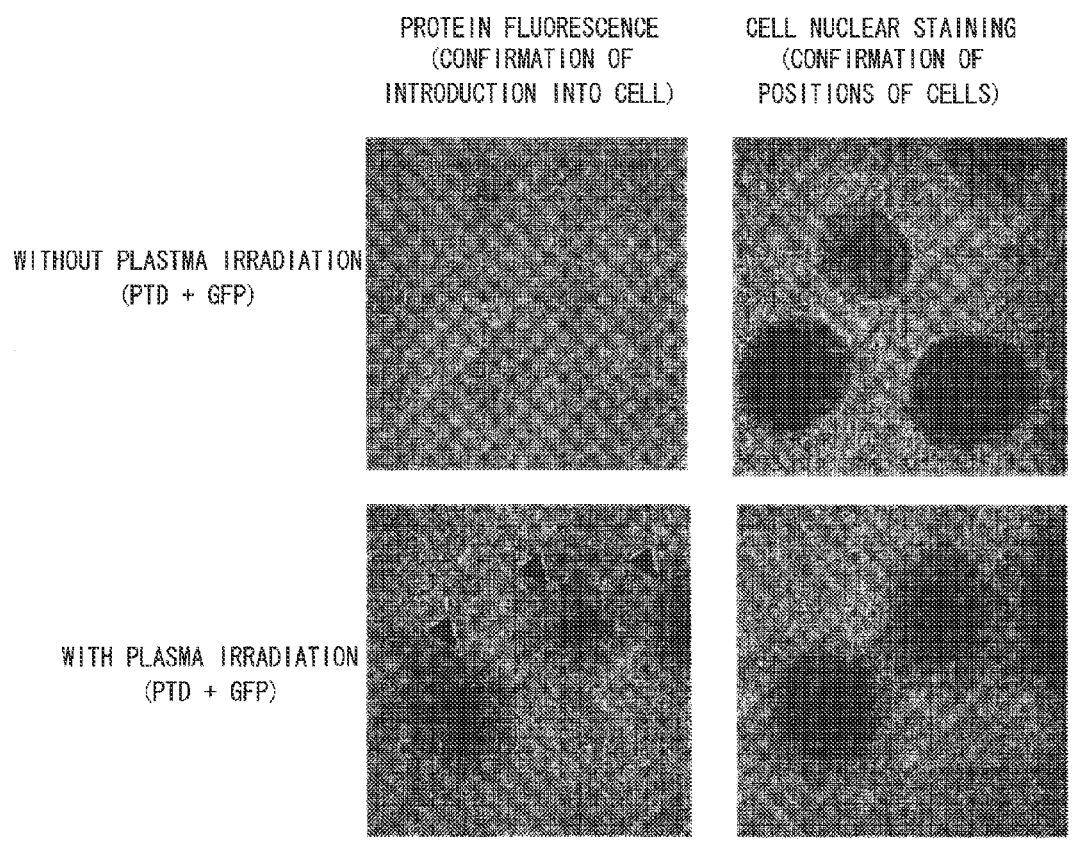
FIG. 5 is an explanatory illustration showing results of tests for introducing a protein into a cell.

The results of investigations of the cells of the test samples 1 and 3 irradiated with the plasma jet are shown in FIG. 5. The results revealed that no fluorescence derived from GFP was detected (upper left picture) in the test sample 3 at the position of the cell confirmed by the cell nuclear staining (upper right picture). On the other hand, the fluorescence derived from GFP was detected (lower left picture) at the position of the cell confirmed by the cell nuclear staining (lower right picture).

The above results indicate that the presence of the damage preventing component can improve the survival rate of the cells after the substance introduction upon the plasma irradiation of the cells for the purpose of the introduction of the target substance (the target protein as used herein) into the cell. Further, the irradiation with the plasma jet demonstrates an efficient cell introduction of the protein with the PTD added.

In order to confirm the accurate amount of the protein introduced into the cell, an amount of the PTD-connected GFP (or GFP) introduced into the cells is measured by flow cytometry and compared.

This comparison revealed that the amount of the PTD-connected GFP introduced into the cells of the test sample 1 which was irradiated with the plasma jet was approximately 1.5-fold more than the cells of the test sample 1 which was not irradiated with the plasma jet. Further, it was found that the cells of the test sample 1 irradiated with the plasma jet using the PTD-connected GFP contained an approximately 1.2-fold amount of the proteins more than the cells of the test sample 3 irradiated with the plasma jet using GFP.

As described above, the liquid culture medium for the substance introduction according to an working example of the present invention can increase the survival rate of the cells after the substance introduction as much as possible upon the plasma irradiation for the purpose of the introduction of the target substance into the cell. Further, the method for the substance introduction into the cell according to a working example of the present invention can introduce the protein of interest into the cell in an efficient fashion by adopting the plasma irradiation device as constructed above.

(Variant Example of a Plasma Irradiation Device)

A description will be made regarding a plasma irradiation device B according to a variant example by reference to FIG. 6.

Figure 6:
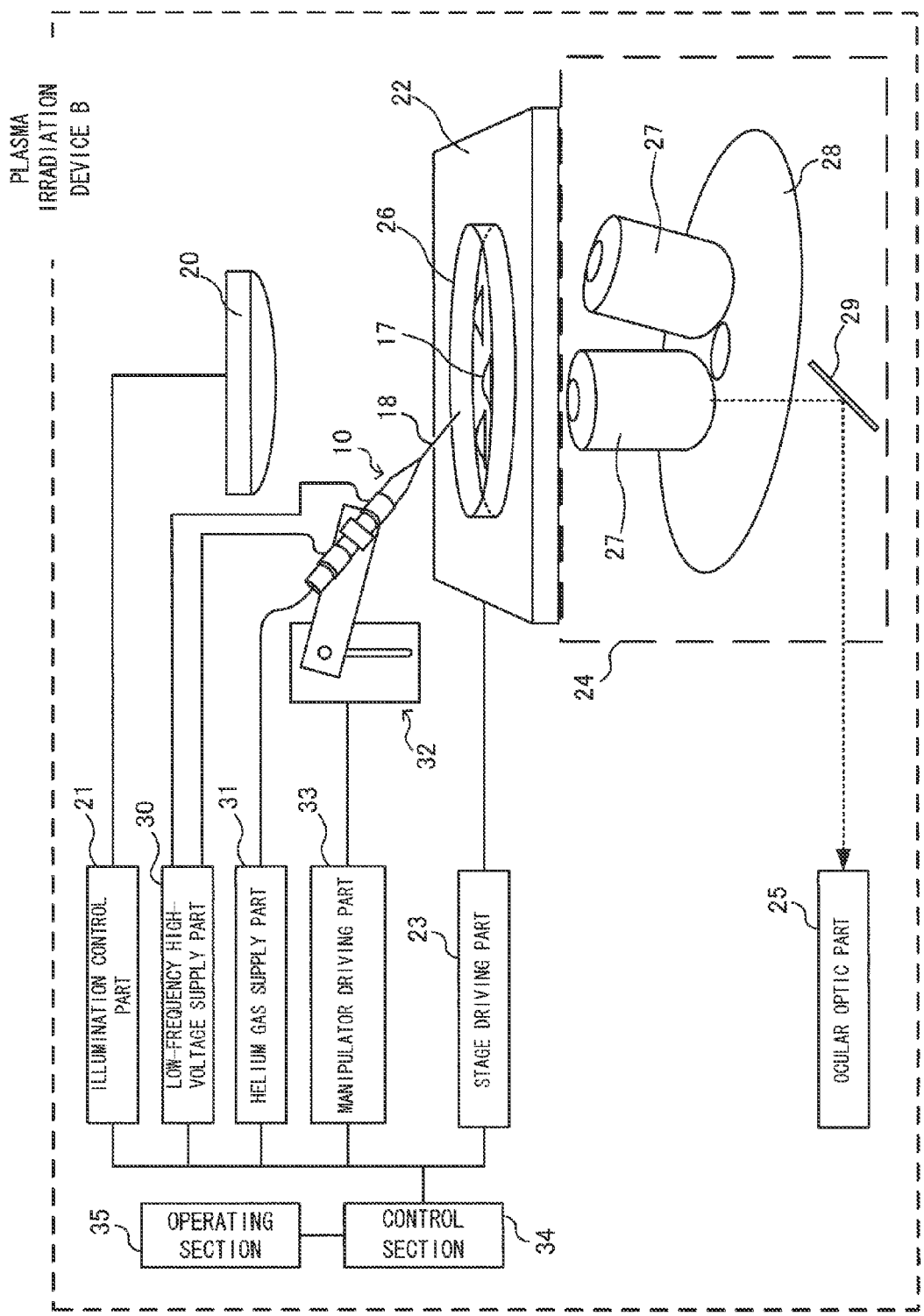
FIG. 6 is an explanatory illustration showing a structure of a plasma generator.

As shown in FIG. 6, the plasma irradiation device B according to the variant example comprises a microscope section acting as the observation section for observing cells 17 with a culture container 26, a plasma generation section for generating a plasma jet 18, a micromanipulator section for supporting the plasma generation section movably in a three-dimensional direction, and a control section 34.

The microscope section comprises an illumination part 20 for illuminating a test object with a ray of light, an illumination control part 21 for adjusting an amount of light outgoing from the illumination part 20, a stage part 22 for placing the culture container 26 containing cells 17 as a test object, a stage driving part 23 for moving the stage part 22 in up-and-down, left-and-right and front-and-back directions, and an object optic part 24 which a ray of light from the test object of interest strikes, and an ocular optic part 25 through which the ray of light outgoing from the object optic part 24 strikes the eyes of a user.

The illumination part 20 is disposed so as to emit a ray of light for illuminating the test object of interest and is equipped with a light source from which, for example, a white light emits. The illumination part 20 may be built-in with a light source for emitting an excitation light for activating a predetermined substance, as needed.

The illumination part 20 is also connected electrically to the illumination control part 21 so as to change an amount of light outgoing from the light source or a kind of the light source by controlling the illumination control part 21.

The stage part 22 is a place on which the culture container 26 such as a culture dish with cultured cells fixed thereon is set. The stage part 22 is provided at its central portion with a hole (not shown) leading the light outgoing from the test object to the object optic part 24, through which the cells and the plasma jet 18 can be visually observed.

The stage part 22 is also connected electrically to the stage driving part 23 and is constructed so as to be movable in up-and-down, left-and-right and front-and-back directions by a stage moving mechanism (not shown).

The object optic part 24 comprises plural number of object lenses 27 and 27 having each a different magnification, a disk-shaped object lens rotating table 28 aligning the object lenses 27 and 27, and a mirror 29 leading the light striking the predetermined object lens 27 to the ocular optic part 27. The mirror 29 may preferably have a wavelength-selectivity. For instance, the mirror 29 may be adjusted in such a manner that the visual light can be reflected but the ultraviolet rays radiated from the plasma jet 18 cannot be reflected failing to lead the light to the ocular optic part 25. By constructing the mirror 29 in the manner as described above, the eyes of the user can be protected from being damaged by the ultraviolet rays radiating from the plasma jet.

The ocular optic part 25 is constructed in such a manner that the light outgoing from the object optic part 24 is sent with a predetermined exit pupil by refracting the light with a lens or the like forming an image of the test object on the retina of the user with a predetermined magnification.

The microscope part is constructed in such a manner as described above to be able to observe the cells within the culture container.

The plasma generation section comprises the electrode section 10, a low-frequency high-voltage supply part 30 and a helium gas supply part 31. As the construction of the plasma generation section is substantially the same as those shown in FIGS. 3 and 4, a description regarding the construction of the plasma generation section is omitted herein.

The micromanipulator section comprises an arm part 32 for supporting the electrode section 10 movably, and a manipulator driving part 33 for driving the arm part 32.

The arm part 32 is driven in accordance with a drive signal from the manipulator driving part 33 for accurately moving the electrode section 10 supported by the arm part 32 in a three-dimensional direction.

The illumination control part 21, the low-frequency high-voltage supply part 30, the helium gas supply part 31, the manipulator driving part 33 and the stage driving part 23 are connected electrically to the control section 34.

The control section 34 is further connected to an operating section 35 for receiving instructions by an action from the user, and devices connected to the control section 34 are constructed so as to be operated by an input of the operation by the user.

By constructing the plasma irradiation device B in the manner as described above, the substance of interest can be introduced into the cell at a pin point while observing the predetermined cell.

(Variant Example 1 of Electrode Section)

Figure 7:
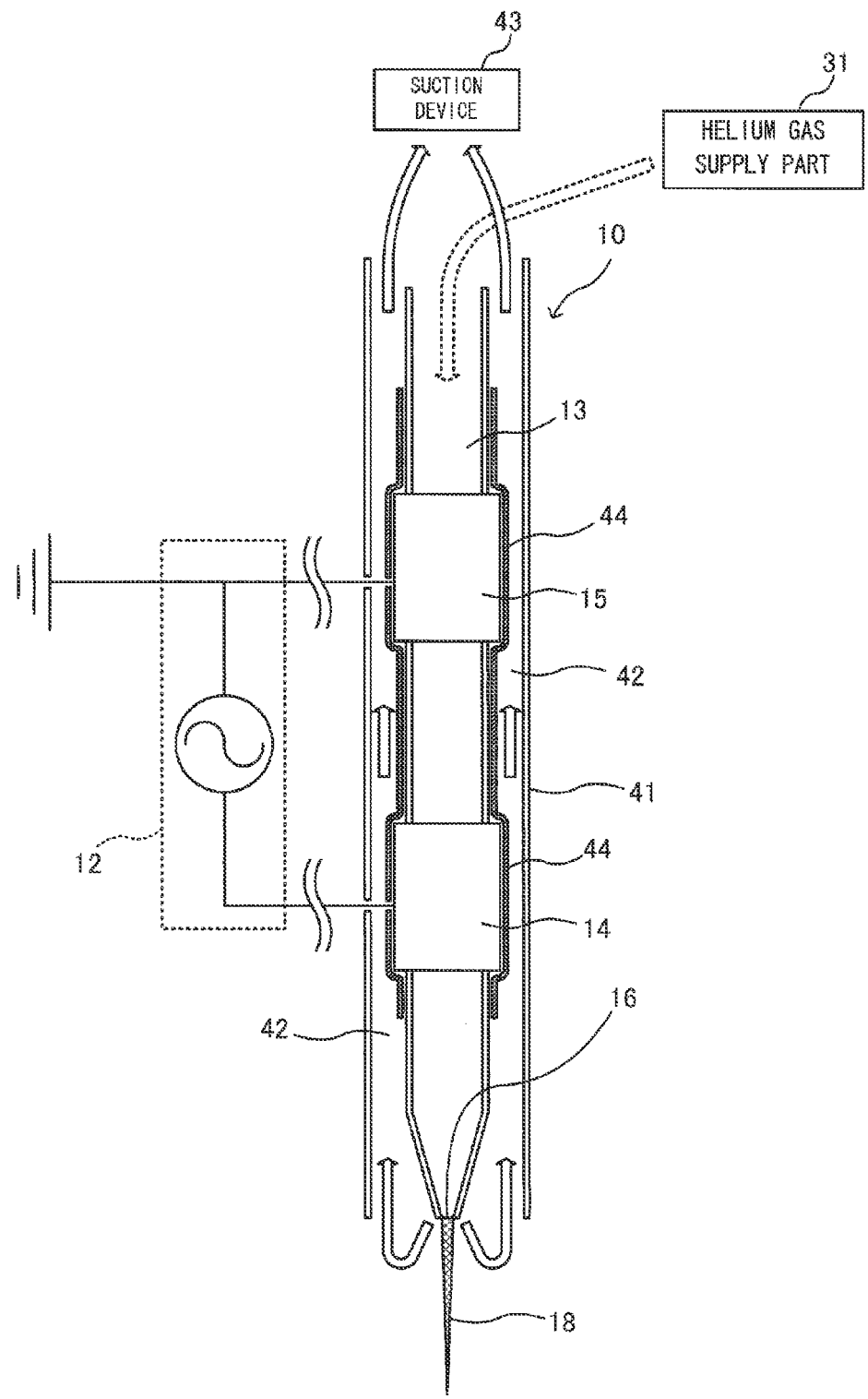
FIG. 7 is an explanatory illustration showing a structure of an electrode section according to a variation of the present invention.

A variant example of the electrode section will be described hereinafter by reference to FIG. 7. As shown in FIG. 7, the electrode section 10 has substantially the same construction as described above, with the exception that it is provided with a suction tube 41 of a double tube type on an outer periphery of the tube member 13. In the description that follows, the similar construction of the electrode section 10 described above will be provided with the identical reference numerals and accordingly a description thereof will be omitted hereinafter.

More specifically, the tube member 13 is provided with a suction tube passage 42 between the outer peripheral surface thereof and an inner peripheral surface of the suction tube 41. The suction tube passage 42 is connected to a suction device 43 and constructed so as to suck helium gas diffusing excessively from the opening 16. Each of the electrodes 14 and 15 as well as the tube member 13 are provided at their outer peripheral surfaces with insulating coverings 44 protecting an insulation between the electrodes 14 and 15 and the tube member 13 from being broken. As the insulation coverings 44, there may be preferably used a thermally shrinkable tube having insulation properties or the like.

With the electrode section constructed in the manner as described above, the noble gas emitting from the opening 16 can be controlled so as not to strike the cell in an excessive amount because an excessive amount of helium gas does not diffuse.

(Variant Example 2 of Electrode Section)

Figure 8:
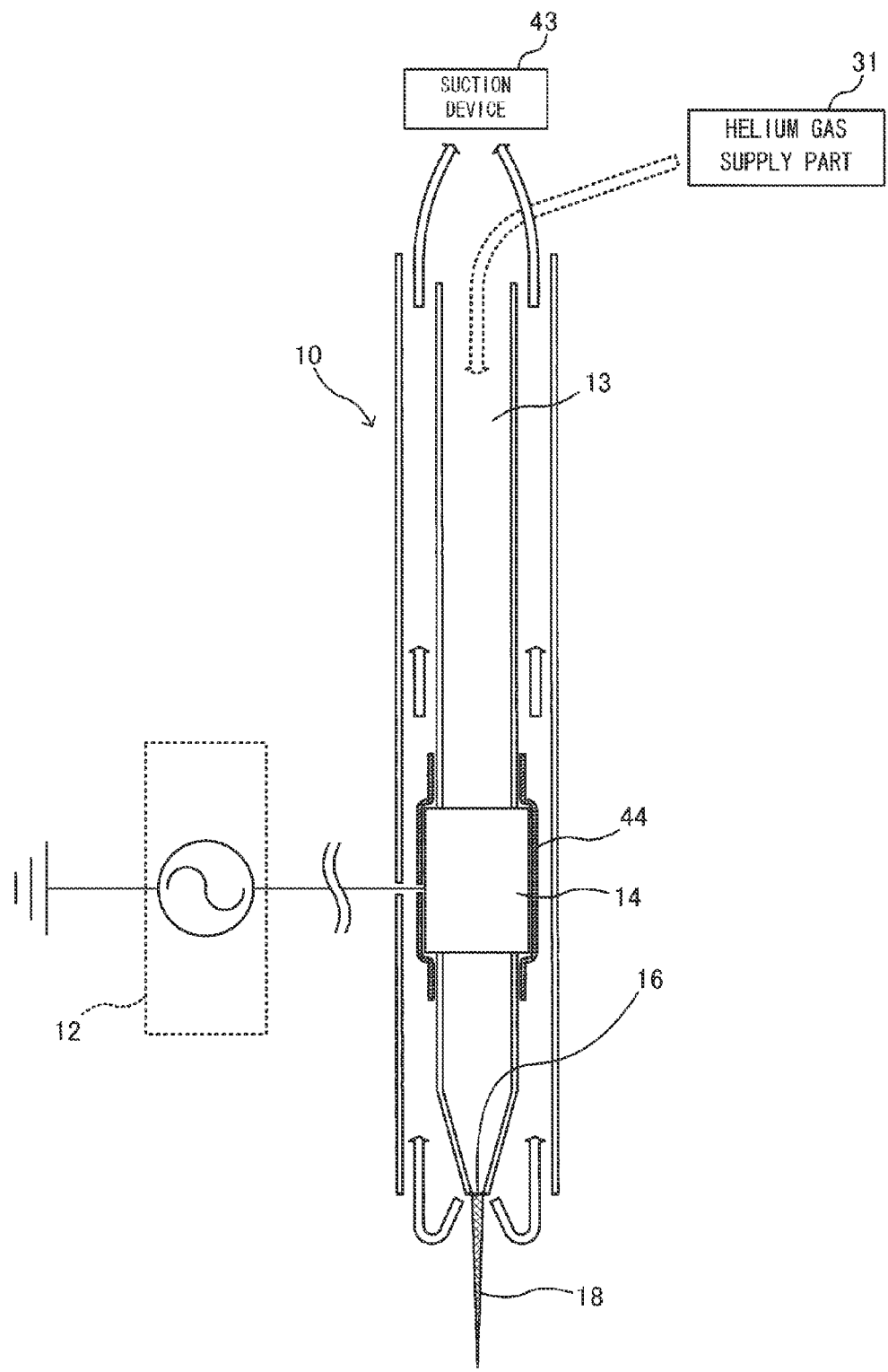
FIG. 8 is an explanatory illustration showing a structure of an electrode section according to a variation of the present invention.

A variant example of the electrode section will be described hereinafter by reference to FIG. 8. As shown in FIG. 8, an electrode section 50 has substantially the same construction as the electrode section 40 as described above, with the exception that it differs therefrom that the first electrode 14 is disposed solely on the tube member 13.

With the electrode section constructed in the manner as described above, the plasma jet may also flow in the upstream direction of the first electrode 14 against a flow of helium gas, however, the plasma jet 18 can also be emitted from the tip of the opening 16.

As described as above, the liquid culture medium for the substance introduction according to a working example of the present invention comprises a liquid culture medium for introducing the predetermined target substance into a cell, which allows the target substance to be introduced into the cell in the liquid culture medium containing the target substance by irradiating the cell with the plasma jet and which can increase the survival rate of the cells after the substance introduction as much as possible upon the irradiation with the plasma jet for the purpose of the introduction of the target substance into the cell because the liquid culture medium contains the damage preventing component capable of preventing the cells from being damaged by the plasma jet.

The method for the substance introduction into the cell according to a working example of the present invention can increase the survival rate of the cells after the substance introduction as much as possible because the cells in the culture container supplied with the liquid culture medium described in any of the embodiments 1 to 4 containing the predetermined target substance are irradiated with the plasma jet and the target substance is introduced into the cells.

The use of the plasma irradiation device B for irradiating the cells 17 in the culture container 26 with the plasma jet 18 enables the introduction of the substance of interest into the cell at a pin point while observing the predetermined cell because the plasma irradiation device B comprises an observation section (a microscope section) for observing the cells 17 within the culture container 26, the plasma generation section for generating the plasma jet 18, and the micromanipulator section for supporting the plasma generation section movably in a three-dimensional direction.

In accordance with the present invention, the cells 17 in the solution containing the protein with the protein-transduction domain (PTD) are irradiated with the plasma jet 18 at atmospheric pressure in a non-thermal equilibrium to introduce the protein into the cell 17, thereby improving an efficiency of introduction of the protein into the cells dramatically.

In conclusion, it is to be noted herein that the description of each of the working examples of the present invention as described above is solely illustrative of the present invention and the present invention is not construed in any respect as being limited to those working examples. It is further noted herein as a matter of course that any modifications including design changes and so on that do not depart from the technical concept of the present invention are encompassed within the scope of the present invention.

For instance, the plasma irradiation device in the previous example is provided with the microscope section as one example of the observation section, but it is not limited to that construction and it may be arranged so as for the user to be able to observe the cells visually.

As an example of the plasma irradiation device, the plasma irradiation device in the previous working example is provided with the microscope section, the plasma irradiation section and the micromanipulator section. However, it is not limited to this construction.

For instance, it may be shaped in the form of a catheter which can be inserted into the human body, whose tip is provided with the electrode section as described above and through which the predetermined substance can be introduced into the cells of the human body. This construction also enables a direct treatment of the diseased part located at the depths of the human body which have so far been difficult to treat.

EXPLANATION OF REFERENCE NUMERALS AND SYMBOLS

10 Electrode section
11 Helium gas supply section
12 Low-frequency high-voltage electric source
13 Tube member 14 First electrode
15 Second electrode
16 Opening
17 Cell
18 Plasma jet
24 Object optic part
25 Ocular optic part
26 Culture container
27 Object lens
33 Manipulator deriving section
34 Control section
A Plasma generator
B Plasma irradiation device

The invention claimed is:

1. A plasma irradiation device for substance introduction for introducing a predetermined target substance into a cell by irradiating the cell in a culture container having a liquid culture medium containing said predetermined target substance with a plasma jet, wherein:

said plasma irradiation device comprises a stage section for supporting said culture container; a microscope section for observing cells in said culture container; a plasma generation section for generating said plasma jet; and a micromanipulator section for supporting said plasma generation section movably in a three-dimensional direction;

wherein said microscope section further comprising a mirror and a predetermined object lens, wherein the mirror is downstream of the predetermined object lens, and the mirror is configured such that ultraviolet rays of the light incoming from the predetermined object lens are not led to an ocular optic part and said plasma generation section comprises a tube member composed of a tubular dielectric with its tip portion tapered off to a point and configured to allow a gas stream to flow therethrough, wherein said tube member is provided with a suction tube in a double tube style at its outside so as to enable a suction of said gas stream diffusing in an excessive amount from the opening at the tip portion of said tube member by means of a suction device connected to said suction tube, thereby preventing the cells from being damaged by the gas stream emitted from said opening at the tip portion thereof; and a double pole electrode disposed on an outer peripheral portion of said tube member, wherein said plasma generation section is configured such that, while flowing a gas stream containing a noble gas as a major component with oxygen mixed therewith through inside of said tube member, and sending a low-frequency high-voltage to each of the electrodes, an electric discharge is caused within the inside of said tube member and emits a plasma jet at a non-thermal equilibrium from an opening at the other end of said tube member, and is further configured such that said gas stream diffusing in an excessive amount from the opening at the tip of said tube member is sucked by a suction device connected to a suction tube part, whereby said predetermined target substance of interest may be introduced into the cell at a pin point by observing the cell by said microscope section while preventing the liquid culture medium from being infected with microorganisms by the production of free radicals upon introducing said target substance into said cell.

2. The plasma irradiation device as claimed in claim 1, wherein said gas stream is mixed with oxygen at a rate of 0.1 to 10%.

3. A substance introduction method for the introduction of a predetermined target substance into a cell at a pin point by observing the cell by a microscope section while preventing a liquid culture medium from being infected with microorganisms by the production of free radicals upon introducing said target substance into said cell, said method comprising the steps of:

(a) providing a plasma irradiation device which comprises a stage section for supporting a culture container; a microscope section for observing cells in said culture container; a plasma generation section for generating said plasma jet; and a micromanipulator section for supporting said plasma generation section movably in a three-dimensional direction; wherein said microscope section further comprising a mirror and a predetermined object lens, wherein the mirror is down stream of the predetermined object lens, and the mirror is configured such that ultraviolet rays of the light incoming from the predetermined object lens are not led to an ocular optic part and said plasma generation section comprises a tube member composed of a tubular dielectric with its tip portion tapered off to a point and configured to allow a gas stream to flow therethrough, wherein said tube member is provided with a suction tube in a double tube style at its outside so as to enable a suction of said gas stream diffusing in an excessive amount from the opening at the tip portion of said tube member by means of a suction device connected to said suction tube, thereby preventing the cells from being damaged by the gas stream emitted from said opening at the tip portion thereof; and a double-pole electrode disposed on an outer peripheral portion of said tube member, wherein said plasma generation section is configured such that, while flowing a gas stream containing a noble gas as a major component with oxygen mixed therewith through inside of said tube member, and sending a low-frequency high-voltage to each of the electrodes, an electric discharge is caused within the inside of said tube member and emits a plasma jet at a non-thermal equilibrium from an opening at the other end of said tube member, and is further configured such that said gas stream diffusing in an excessive amount from the opening at the tip of said tube member is sucked by a suction device connected to a suction tube part, (b) providing a cell, (c) providing as a target substance a polypeptide or an antibody, which polypeptide or antibody is connected to a transmembrane signal sequence for facilitating transduction of a cell membrane, and (d) irradiating the cell with a plasma jet emitting from said plasma irradiation device, thereby introducing said target substance of interest into the cell at a pin point by observing the cell by said microscope section while preventing the liquid culture medium from being infected with microorganisms by the production of free radicals upon introducing said target substance into said cell.

4. The substance introduction method as claimed in claim 3, wherein said liquid culture medium for the substance introduction contains fetal bovine serum having an absorbance at a wavelength of 200 nm to 300 nm as a damage preventing component capable of preventing said cell from damages caused by ultraviolet rays derived from said plasma jet.

* * * * *